US008950866B2

(12) United States Patent
Volkwardt et al.

(10) Patent No.: US 8,950,866 B2
(45) Date of Patent: Feb. 10, 2015

(54) PROCESS FOR RELIABLY DETERMINING THE AXIAL LENGTH OF AN EYE

(71) Applicant: Carl Zeiss Meditec AG, Jena (DE)

(72) Inventors: Martin Volkwardt, Kroeslin (DE); Ferid Bajramovic, Jena (DE); Ralf Ebersbach, Schmoelln (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 14/033,544

(22) Filed: Sep. 23, 2013

(65) Prior Publication Data

US 2014/0092363 A1 Apr. 3, 2014

Related U.S. Application Data

(60) Provisional application No. 61/706,997, filed on Sep. 28, 2012.

(30) Foreign Application Priority Data

Sep. 28, 2012 (DE) .......................... 10 2012 019 467

(51) Int. Cl.
 A61B 3/00 (2006.01)
 A61B 3/14 (2006.01)
 A61B 3/10 (2006.01)
(52) U.S. Cl.
 CPC ............... *A61B 3/102* (2013.01); *A61B 3/1005* (2013.01)
 USPC ........... 351/246; 351/200; 351/206; 351/210; 351/221

(58) Field of Classification Search
 USPC ......... 351/246, 247, 200, 205–206, 208–210, 351/221–223
 See application file for complete search history.

(56) References Cited

U.S. PATENT DOCUMENTS

| 5,321,501 A | 6/1994 | Swanson et al. |
| 2011/0299034 A1* | 12/2011 | Walsh et al. .................. 351/206 |
| 2013/0242259 A1* | 9/2013 | Hacker et al. .................. 351/206 |
| 2013/0301009 A1 | 11/2013 | Hacker et al |

FOREIGN PATENT DOCUMENTS

| DE | 102010051281 A1 | 5/2012 |
| EP | 0928596 A1 | 7/1999 |

OTHER PUBLICATIONS

W. Haigis, "Optical Coherence Biometry", Modern Cataract Surgery, T. Kohnen, Ed. Basel, Karger Publishers, Dec. 2002, vol. 34, p. 119-130, Germany.
Haag-Streit AG, "Biometry Connected . . . " Jun. 2010, Switzerland.

* cited by examiner

*Primary Examiner* — Dawayne A Pinkney
(74) *Attorney, Agent, or Firm* — Leydig, Voit & Mayer, Ltd.

(57) ABSTRACT

A method for reliably determining the axial length of an eye uses optical coherence tomography (OCT), where the eye is aligned with a fixation mark so that the optical axis of the measuring instrument coincides at least approximately with a visual axis of the eye. The axial length is determined from at least one B-scan taken in an initial AS mode (anterior segment mode) and the axial length is also determined from at least one B-scan taken in a second RS mode (retina segment mode). A resultant reliable axial length of the eye is determined using the axial lengths from the AS and RS modes, where available and where possible, or the process is ended without a resultant axial length.

13 Claims, 3 Drawing Sheets

PROCESS FOR RELIABLY DETERMINING THE AXIAL LENGTH OF AN EYE

CROSS REFERENCE TO RELATED APPLICATIONS

This application claims priority from German Patent Application No. 10 2012 019 467.6 filed Sep. 28, 2012 and U.S. Provisional Patent Application No. 61/706,997, filed Sep. 28, 2012 , both of which are hereby incorporated by reference herein in their entireties.

FIELD

The present invention relates to a process for determining the axial length of an eye using optical coherence tomography (OCT), two-dimensional scans (B-scans) being obtained in different measuring modes.

BACKGROUND

An important application is the pre-operative selection of intraocular lenses in the treatment of cataracts. The most important measurement for this selection is the axial length of the eye from the front of the cornea to the retina. In the prior art this is preferably carried out using non-contact optical interferometry processes, which are known as PCI (partial coherence interferometry) or OCT (optical coherence tomography). In these processes, structural interfaces can be represented as one-dimensional depth profiles (A-scans) or as two-dimensional cross-sectional views (B-scans), specular reflexes on the optical boundary surfaces and/or light that is scattered in the different media of the eye being detected.

In both measurement processes it is important for the measurement to be taken along an axially oriented axis corresponding to the visual axis. Otherwise, mistakes can arise during the choice of IOL so that the patient's vision is significantly impaired after implantation of the IOL.

In order to guarantee, with a high level of reliability, that the measurement is along the visual axis, in the prior art, the patient is offered a fixation light to fixate on while the measurement is being taken with the optical measuring instrument. This aligns the visual axis of the eye with the main measuring axis of the instrument (instrument axis), which also corresponds to the Z-axis of the measuring instrument's coordinate system. This can be found in the literature (ISO/CD 19980, "Ophthalmic instruments—Corneal topographers." 2009). If the instrument axis is aligned with the visual axis, then, in most cases, the cornea and the retina are sufficiently vertical to the main measuring axis, so that the measuring beams reflected by the cornea and the retina are accurately registered by the measuring instrument.

According to a first method described in the literature (W. Haigis, "Optical Coherence Biometry," in Modern Cataract Surgery, T. Kohnen, Ed. Basel: Karger Publishers, 2002, pp. 119-130), the axial length is measured by partial coherence interferometry using the double-path method. In this method two beams with different optical path lengths fall into the eye and are specularly reflected at the front of the cornea and the retina to produce interference. The eye length can be determined from the signals at different optical path lengths. Since a usable signal is only obtained if there is a specular reflex from both the cornea and the retina, this process has the advantage that the cornea and the retina must be approximately vertical to the measuring beam and therefore to the instrument axis in order to generate a distance signal.

It has been demonstrated experimentally that, under these measuring conditions which produce a usable distance signal, the instrument axis/measuring axis is approximately identical to the visual axis and corresponds to the axial length distance measured along the instrument axis, which is crucial for calculating the IOL.

This measuring process therefore virtually excludes the possibility of obtaining a false reading for eye length, if the optical axis deviates too much from the instrument axis, and then using this for calculating the IOL.

However, a disadvantage is that it relies upon a minimum amount of cooperation from the patient to fixate his/her gaze during the measurement and, if this is not forthcoming, no measurements, or very few, and therefore statistically less valid, readings of the axial eye length, can be determined Another disadvantage is that it is difficult to obtain B-scan readings or anterior chamber depth measurements, since, because of the angle of the measuring beam relative to the interfaces, either the cornea or the lens fails to produce a specular reflex that can be registered by the device in these measurements. Therefore newer methods, which promise a higher degree of reliability in the selection of intraocular lenses and require measurement of the anterior chamber depth, lens thickness or lens radius, cannot be used or can only be used with difficulty.

According to a second method described in the literature (Haag-Streit AG, "Biometry Connected . . . " June 2010), the intraocular distances are measured by means of one or more so-called B-scans, obtained by optical coherence tomography. This can be used to resolve not only the front surface of the cornea and the retina but also other tissue structures. For example, cornea thickness, anterior chamber depth and/or lens thickness can be determined.

The basic principle of the OCT method, described for example in U.S. Pat. No. 5,321,501 A, is based on white light interferometry and compares the duration of a signal using an interferometer (usually a Michelson or Mach-Zehnder interferometer). There the arm of known optical path length is used as an object-external reference to the measuring arm. The interference of the signals from both arms produces a pattern, from which the relative optical path length within an A-scan (single depth signal) can be deduced. In a one-dimensional raster scan, the beam is then directed transversely in one or two directions, allowing the recording of a two-dimensional B-scan or a three-dimensional tomogram. This produces sufficient signals even in the B-scan, because this process records both specular reflexes and also diffusion in the object.

However, unlike the double path method, the measuring principle of these processes does not in itself guarantee that the axial length (axial length of the eye) will be measured along the correct axis (visual axis), which is important for calculating the intraocular lenses. This is because a recording and a signal can still be obtained, even though the measuring beam is not vertically incident upon the front surface of the cornea or not aligned with the visual axis. Measurement along the instrument axis then provides an A-scan, which in itself does not appear to be defective, even if it was not measured along the visual axis due to poor fixation. However, in general, deriving the axial length from the measurement along the instrument axis would result in incorrect, systematically shortened readings, since, if the measuring instrument is not properly aligned with the visual axis because of eye movement or poor fixation, the A-scan measures too far off the visual axis and, with a typically convex eye, this results in a shortening of the cornea to retina distance.

Generally there is also the problem of the lateral matching of the B-scan to the eye. If the eye is moved during the measurement itself or even during alignment of the measuring instrument on the eye, this results in incorrect measurements due to inaccurate alignment.

If these eye movements are not taken into consideration, a B-scan and the intraocular distances derived from it are laterally displaced relative to the eye and are therefore incorrectly assigned. There is therefore no guarantee that the A-scan measures along the instrument axis or that the A-scan within a B-scan running along the instrument axis actually measures the eye length. Moreover, even if they are accurately aligned, only a few A-scans—that is to say only those along the instrument axis—can be used for calculating the axial length, so that the measured axial length is associated with a relatively high degree of statistical uncertainty.

A further process for determining the distances between localised interfaces in the eye is described in DE 10 2010 051 281 A1. Using the scans taken under different conditions, which scans include at least two of the interfaces present in the eye, a parametric eye model can be appropriately adjusted by a control and evaluation unit to allow model-based determination of the eye biometry.

However, even with this solution, the automatic evaluation of A and B-scans to obtain biometric data is faced with the problem of a large number of measuring situations and disturbances. These include, for example, attenuation of the measuring beam by cataracts or defocusing of the measuring beam due to refractive errors or the presence of pathological conditions.

SUMMARY

In an embodiment, the present invention provides a method for reliably determining the axial length of an eye uses optical coherence tomography (OCT), where the eye is aligned with a fixation mark so that the optical axis of the measuring instrument coincides at least approximately with a visual axis of the eye. The axial length is determined from at least one B-scan taken in an initial AS mode (anterior segment mode) and the axial length is also determined from at least one B-scan taken in a second RS mode (retina segment mode). A resultant reliable axial length of the eye is determined using the axial lengths from the AS and RS modes, where available and where possible, or the process is ended without a resultant axial length.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1:
FIG. 1 shows a B-scan taken in AS mode.

In an embodiment, the present invention provides a process for reliably determining the axial length of the eye, which overcomes the disadvantages of the solutions known from the prior art and ensures that only readings recorded with the most accurate possible alignment of the main measuring axis of the instrument and the visual axis of the patient's eye are used for determining the axial eye length.

In an embodiment, the present invention provides a process for reliably determining the axial length of an eye using optical coherence tomography (OCT), where the eye is aligned with a fixation mark so that the optical axis of the measuring instrument coincides at least approximately with the visual axis of the eye, in that, in keeping with the process steps:

a) the axial lengths are determined from at least one B-scan in a first AS mode (anterior segment mode), c) the axial lengths are determined from at least one B-scan in a second RS mode (retina segment mode), the aggregated axial lengths from AS and RS modes are used, if available and where possible, to determine a reliable resultant axial eye length or to end the process without a resultant axial length.

Preferably a plurality of B-scans are carried out in each of the two modes and, in the process steps:

b) the axial lengths determined in AS mode are aggregated, d) the axial lengths determined in RS mode are similarly aggregated, outliers being detected before aggregation of the axial lengths.

The present invention relates to a process for determining the axial length of an eye, particularly for use in biometric ophthalmic instruments. The axial length of the eye from the front surface of the cornea to the retina is the most important reading for the preoperative selection of intraocular lenses in the treatment of cataracts.

In the process according to an embodiment of the invention for reliably determining the axial length of an eye by optical coherence tomography (OCT), the eye is aligned with a fixation mark, so that the optical axis of the measuring instrument coincides at least approximately with the visual axis of the eye. After this, according to the steps of this process:

a) the axial lengths are determined from at least one B-scan taken in an initial AS mode (anterior segment mode) and c) the axial lengths are determined from at least one B-scan taken in a second RS mode (retina segment mode).

During the measurements, two-dimensional OCT cross-sectional views, so-called B-scans are recorded, first in AS mode (anterior segment mode) and immediately afterwards in RS mode (retina segment mode). Axial length readings of the examined eye can be determined from the B-scans from both measuring modes. Depending upon availability, the axial lengths from AS mode and RS mode are used where possible to determine a reliable resultant axial eye length or to end the process without a resultant axial length. Determination of axial lengths using process steps a) and c) can be carried out in any order, one immediately after the other or simultaneously.

According to a first advantageous configuration, a plurality of B-scans are completed in both modes and in the process steps:

b) the axial lengths determined in AS mode are aggregated and d) the axial lengths determined in RS mode are similarly aggregated, outliers being detected before aggregation of the axial lengths.

Experience has shown that the reflexes arising from the retinal tissue structures do not arise directly on their surface but, depending upon the measuring process used, in different layers beneath the surface of the retina.

Whilst ultrasound waves, for example, are reflected by the so-called "internal limiting membrane" (ILM) of the retinal tissue structure and generate a detectable reflex, the light beams of OCT-based processes are reflected on the so-called "retinal pigment epithelium" (RPE), which is located deeper in the retinal tissue structures. By means of corresponding specifications for the segmentation of the measurement signals, both the ILM and the RPE can be resolved and detected by OCT-based measurement processes.

Segmentation is an aspect of digital image processing and machine vision. Segmentation refers to the generation of regions with associated content by amalgamating adjacent image regions or even just pixels that meet a certain homogeneity criterion. For example, gradient strength, intensity, signal-to-noise ratio or local entropy can be used as homogeneity criteria for segmentation, either individually or in combination. In the process according to the invention described here, segmentation is used to detect boundary surfaces in the eye.

FIG. 1 shows a B-scan in AS mode, which includes (from right to left) the eye components cornea K, iris I, (phakic) lens L and retinal tissue structures R. The axial lengths in the B-scans taken in AS mode can be determined from the distances between the detected vertex V of the front surface of the cornea and the retinal tissue structures R and there, in particular, the segmented RPE.

Figure 2:
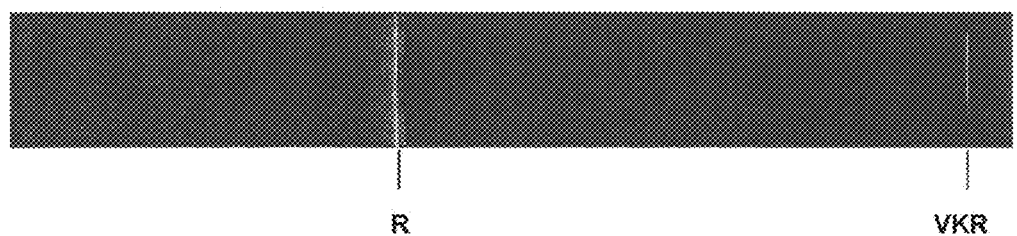
FIG. 2 shows a B-scan taken in RS mode.

In contrast, FIG. 2 shows a B-scan taken in RS mode, clearly showing the retinal tissue structure R next to the so-called vertex/corneal reflex VKR on the right-hand region of the image. In the B-scans obtained in RS mode, the axial lengths are determined from the distances between detected vertex/corneal reflex VKR and the segmented RPE in the retinal tissue structures R.

A plurality of B-scans are taken in each of the two modes to provide a single axial length. The problem then is how to sensibly aggregate these individual axial lengths measured in the two modes to produce a single axis length. This is particularly challenging if the individual axial length measurements differ greatly from each other and are therefore not consistent or if the axial length could not be determined in one of the two modes.

In the process according to the invention, it should be noted that the B-scans performed in AS mode and in RS mode must be carried out immediately after each other, with the shortest possible sequence. This serves to minimise possible eye movements between the measurements.

Moreover, it is possible for the B-scans in the two different modes to be performed with different wavelengths and/or scan conditions and/or optical systems.

According to an embodiment of the invention, axial lengths are determined from the B-scans and aggregated separately for each mode, after detecting outliers. Outliers are detected by defining a range for the expected axial lengths starting from the median of all individual measurements of the eye lengths; readings outside this range represent outliers and are excluded from the aggregation.

The axial lengths determined in the two modes are aggregated by forming the arithmetical mean of the axial lengths remaining after detection of outliers, this only being possible if sufficient, preferably at least 2, axial lengths remain. Otherwise, it is not possible to determine an aggregated axial length for the relevant mode. This can be due to inconsistent axial lengths.

This can be caused, for example, by the absence of retinal signals because the cataract is too thick or the eyelid is (partially) closed. However, it is also possible that a false reflex has been detected in the B-scan in RS mode, caused, for example, by a phakic or pseudo-phakic intraocular lens (IOL).

Figure 3:
FIG. 3 shows a B-scan taken in RS mode with the reflex of an intraocular lens.

In this connection, FIG. 3 shows a B-scan in RS mode with the reflex of an intraocular lens (IOL). (From right to left) the B-scan only includes the reflexes of an intraocular lens IOLR and the segmented RPE of the retinal tissue structure R. If the reflex of the IOLR is incorrectly detected as the vertex/corneal reflex, this leads to incorrect determination of the axial length in RS mode and consequently to inconsistent axial lengths in the two modes—assuming that an axial length measurement is even possible in AS mode. Detection of the reflex of an IOL as a vertex/corneal reflex is usually due to imperfect fixation of the patient and/or imprecise alignment of the measuring instrument relative to the eye during the measurements so that there is no vertex/corneal reflex at all.

The process according to an embodiment of the invention is characterised in that the aggregated axial lengths from AS and RS modes are used, if available and where possible, to determine a resultant reliable axial eye length or to end the process without a resultant axial length, wherein, e) if neither of the two modes provides an aggregated axial length, no value is displayed, f) if only AS mode provides an aggregated axial length, this corresponds to the resultant axial length and is displayed, g) if only RS mode provides an aggregated axial length, this corresponds to the resultant axial length and is displayed, and h) if both modes provide an aggregated axial length and are consistent, an axial length aggregated from both modes or one of the aggregated axial lengths from either RS or AS mode is displayed as the resultant axial length, and if they are not consistent, the axial length aggregated in either RS mode or AS mode is displayed as the resultant axial length.

It is advantageous if the readout displays a warning to show which mode the resultant axial length comes from or that the axial lengths of the two modes are inconsistent or that no value could be determined After the first aggregation phase, in which the axial length from the B-scans of the two different modes are aggregated separately, for the second aggregation phase, in which the aggregated axial lengths from AS and RS modes are to be aggregated to produce a resultant axial length, it is necessary to distinguish between four possible cases and these are explained in more detail below.

In the first case, where neither of the two modes provides an aggregated axial length in accordance with process step e), no value is displayed. The process is ended with a corresponding warning.

In the second case, where only AS mode provides an aggregated axial length in accordance with process step f), this corresponds to the resultant axial length. The process is ended with the readout of the resultant axial length. A warning alerts the user to the fact that the resultant axial length comes from AS mode.

In the third case, where only RS mode provides an aggregated axial length in accordance with process step g), this corresponds to the resultant axial length.

The process is ended with the readout of the resultant axial length. Again a warning alerts the user to the fact that the resultant axial length comes from RS mode.

More advantageously, in a variant and configuration, the RS scans approved for forming the aggregated axial length can be restricted by checking and complying with an acceptable range for vertex/corneal reflexes in the B-scans obtained in RS mode. This is carried out as follows:

A reference value is determined for the axial position of the corneal reflex from the B-scans from AS mode and an acceptable range for vertex/corneal reflex in the B-scans from RS mode is defined from this and used for the repeat or initial aggregation of the axial lengths of the B-scans obtained in RS mode. Readings that are outside the acceptable range are not approved for aggregation purposes, because the detected reflex cannot be guaranteed to correspond to the vertex/corneal reflex. All individual axial length measurements with a detected reflex within the acceptable range are preferably also aggregated with the same outlier detection as in the first aggregation phase.

If different wavelengths of scan illumination and/or optical systems are used for the B-scans in the two different modes, this must be taken into account when determining the reference value and defining the acceptable range for corneal reflex in the B-scans obtained in RS mode. The axial position of the foremost point on the cornea is identified for determining the reference value.

In a further embodiment, it is possible to use real-time B-scans from a live OCT to determine the reference value. The primary purpose of this live OCT is not to obtain axial lengths but, like the AS mode, it provides an image of the anterior eye.

If the AS mode does not provide any axial lengths, or not consistent ones, this matching of the RS scans with the reference value for the axial corneal position from AS mode is particularly important, in order to guarantee that the correct result has been identified for axial length.

This is the case if, for example, it is impossible to measure the axial length in AS mode because of a cataract but it is possible to measure it in RS mode, because of greater sensitivity in the region of the retina. In this case, the accuracy of the axial length measurement in RS mode cannot be effected by comparing it with the axial length measured in AS mode and, as outlined above, a direct examination of the vertex/corneal reflex is required. The same applies if the axial lengths measured in the two modes are inconsistent.

The selection outlined above for aggregating the axial lengths of approved B-scans taken in RS mode via an acceptable range of vertex/corneal reflex defined via the B-scans in AS mode is not only expedient in the context of axial length aggregation. Even if no axial lengths are displayed, an acceptable range defined in this way can be used for selecting the B-scans taken in RS mode that are suitable for further use, for example, for selection of the RS-scans presented.

In the fourth and last case, if, in accordance with process step h), both modes provide an aggregated axial length and are consistent, then an axial length aggregated from the two modes or one of the aggregated axial lengths from RS or AS mode is displayed as the resultant axial length; if they are not consistent, then the axial length aggregated in RS mode or AS mode is displayed as the resultant axial length.

Once again, it is advantageous if the readout shows a warning to indicate whether the axial lengths from the two modes are inconsistent and from which mode the resultant axial length comes.

The consistency of the aggregated axial length from AS and RS mode with each other is checked by ensuring that the difference between both absolute values is within a defined tolerance. This tolerance can correspond to the threshold for outlier detection from the first aggregation phase.

If there is no apparent consistency between the aggregated axial lengths from the two modes, then the axial lengths determined in RS mode are regarded as being more reliable. The axial length measurements from AS mode are discarded and the procedure according to process step g) is followed. Alternatively, a comparative evaluation can be made of the signal quality in both modes to decide whether the axial lengths determined in RS mode or in AS mode are considered to be more reliable.

In general, the axial lengths determined in RS mode are considered to be more reliable, because the lateral resolution of the retinal tissue structures is clearly greater in the B-scan taken in RS mode than those of the B-scan taken in AS mode, and the sensitivity is also greater. Particularly where pathologies are present, the B-scan taken in AS mode can result in incorrect segmentation of the RPE.

Figure 4:
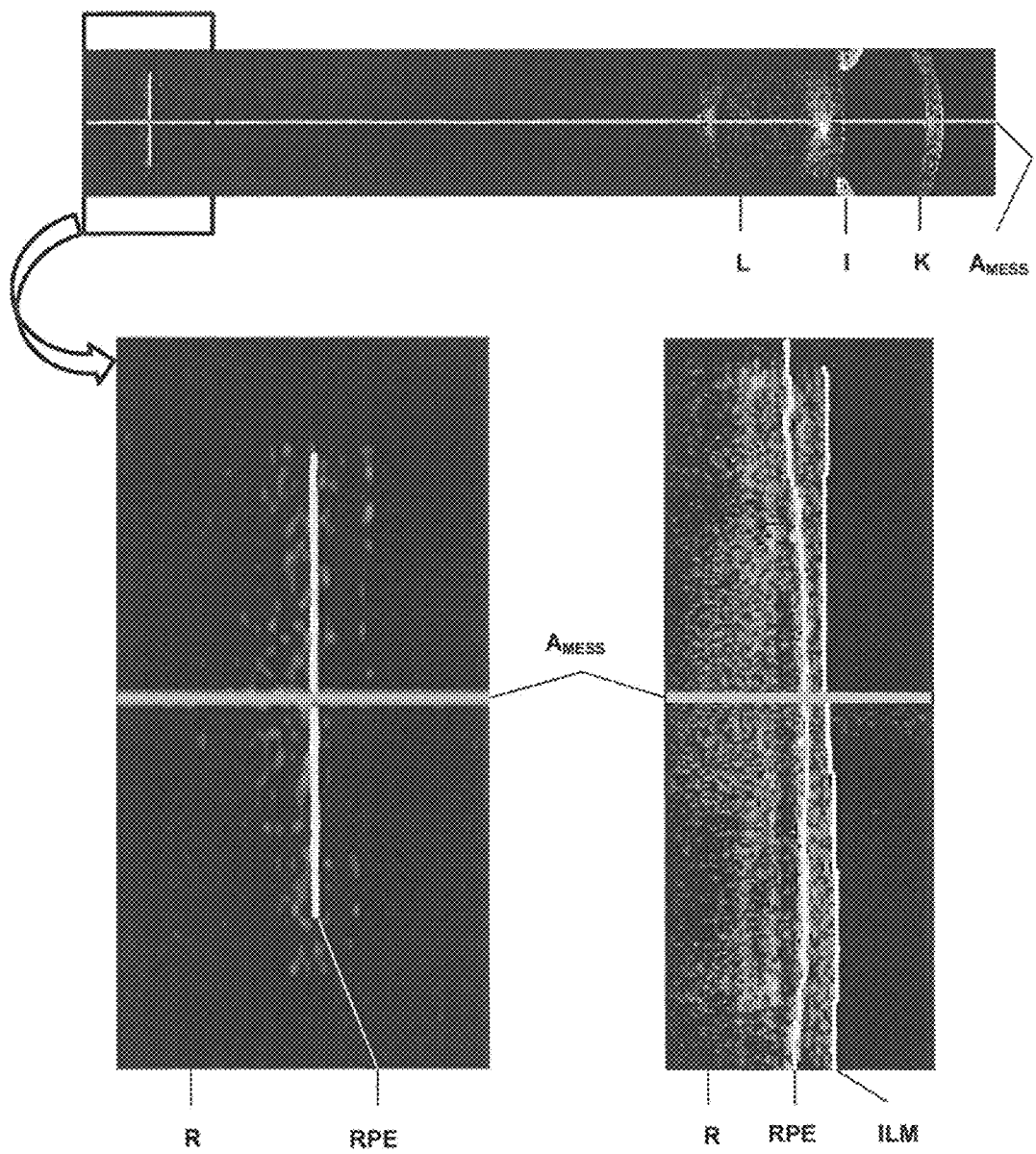
FIG. 4 shows a B-scan taken in AS mode with detail enlargement and an extract from a B-scan of the same eye taken in RS mode and FIG. 5 shows a flowchart of a process according to an embodiment of the invention.

This is illustrated by the B-scan taken in AS mode shown in FIG. 4 with a detail enlargement and an extract from the B-scan of the same eye taken in RS mode.

The top image shows a B-scan taken in AS mode including, along the measuring axis $A_{MESS}$ (from right to left), the components of the eye, cornea K, iris I, (phakic) lens L and retinal tissue structures R. By way of comparison, the bottom image shows a detail enlargement of the retinal tissue structures R.

Whilst the bottom left image, which is a detail enlargement of the retinal tissue structures R, shows the B-scan taken in AS mode, the bottom right image shows by comparison a detail enlargement of the retinal tissue structures R, from the corresponding B-scan taken in RS mode, however.

Because of the poor lateral resolution of the B-scan in AS mode, segmentation of the RPE fails, since the actual RPE is incorrectly interpreted as the ILM. This can be seen in the bottom left image in FIG. 4. In contrast, the retinal tissue structures are accurately resolved in RS mode and both the retinal pigment epithelium RPE and the internal limiting membrane ILM are accurately segmented in the B-scan. This can be seen in the bottom right image in FIG. 4. This effect is intensified if there are pathologies present.

In a variant and configuration of case 4, it is advantageous, as in case 3, to restrict the RS-scans approved for forming the aggregated axial length for RS mode by checking and complying with an acceptable vertex-corneal reflex range in the RS-scans. The definition and use of an acceptable range is outlined in detail in the description of case 3.

Figure 5:
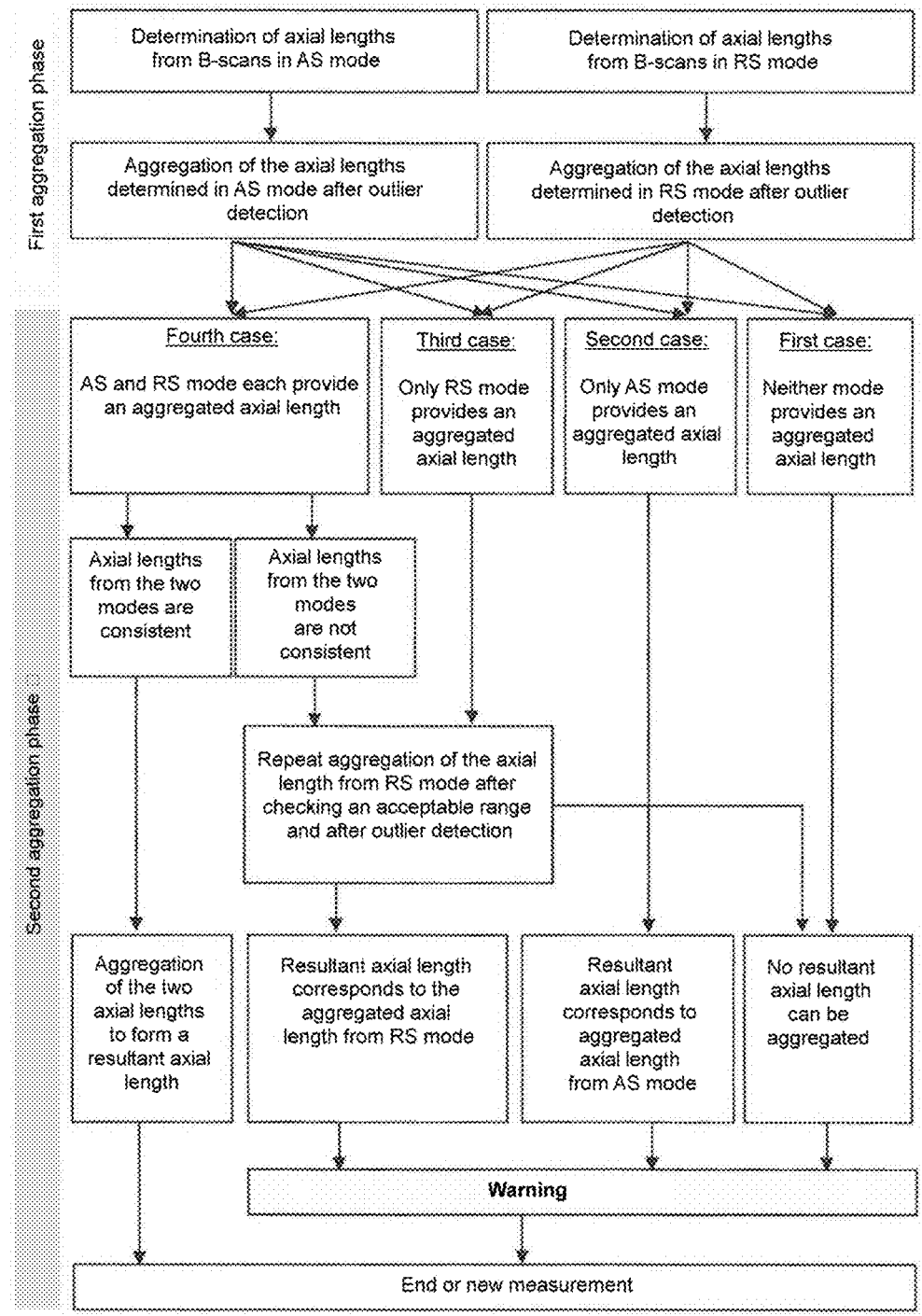

Finally, FIG. 5 shows the process according to the invention clearly in the form of a flowchart.

The present invention provides a process for determining the axial length of an eye, which process would be used particularly in biometric ophthalmic instruments.

The process allows the axial length of an eye to be reliably determined, ensuring that only readings recorded with the most accurate possible alignment of the main measuring axis of the instrument and the visual axis of the patient's eye are used in determining the axial length. It also increases reliability by using two different measuring modes.

The process according to the invention serves to identify the presence of pathological changes and, under certain circumstances, can still allow the axial length to be reliably measured.

The process is also characterised by better cataract penetration, since, in rare cases, a retinal signal is only obtained in RS mode or only in AS mode.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A method for reliably determining the axial length of an eye by optical coherence tomography (OCT) using a measuring instrument, the eye being aligned with a fixation mark so that an optical axis of the measuring instrument coincides at least approximately with a visual axis of the eye, the method comprising:
   a) determining the axial length from at least one B-scan taken in an initial AS mode (anterior segment mode);
   c) determining the axial length from at least one B-scan taken in a second RS mode (retina segment mode); and determining a resultant reliable axial length of the eye using the axial lengths from the AS and RS modes, where available and where possible, or ending the process without a resultant axial length.

2. The method according to claim 1, wherein the axial lengths are determined in accordance with process steps a) and c) in any order, one immediately after the other or simultaneously.

3. The method according to claim 1, wherein a plurality of B-scans are taken in both modes and further comprising:
   b) aggregating the axial lengths determined in AS mode,
   d) aggregating the axial lengths determined in RS mode, and detecting outliers before aggregation of the axial lengths.

4. The method according to claim 1, wherein,
   e) if neither of the two modes provides an aggregated axial length, no value is displayed,
   f) if only AS mode provides an aggregated axial length, this corresponds to the resultant axial length and is displayed,
   g) if only RS mode provides an aggregated axial length, this corresponds to the resultant axial length and is displayed, and
   h) if both modes provide an aggregated axial length and are consistent, an axial length aggregated from the two modes or one of the aggregated axial lengths from either RS or AS mode is displayed as the resultant axial length and if they are not consistent, the axial length aggregated in either RS mode or AS mode is displayed as the resultant axial length.

5. The method according to claim 4, wherein a readout displays a warning to show which mode the resultant axial length comes from or that the axial lengths from the two modes are inconsistent or that no value could be determined.

6. The method according to claim 1, wherein a reference value for the axial position of the corneal reflex is determined from at least one AS mode B-scan and from this an acceptable range for the vertex/corneal reflex is defined in at least one RS mode B-scan for the repeat or initial determination of axial length, readings outside the acceptable range being allowed.

7. The method according to claim 6, wherein a plurality of B-scans are taken in one mode or in both modes and the determined axial lengths are aggregated.

8. The method according to claim 1, wherein the B-scans in AS mode and in RS mode can be performed with different wavelengths and/or scan conditions and/or optical systems.

9. The method according to claim 1, wherein a range of expected axial lengths is defined from a median of all individual measurements of eye length and readings outside this range are outliers and excluded from the aggregation.

10. The method according to claim 3, wherein the axial lengths determined in the two modes are aggregated by forming the arithmetical mean of the axial lengths remaining after detection of outliers, so long as at least 2 axial lengths remain.

11. The method according to claim 6, wherein different wavelengths and/or optical systems used in the mode are taken into account in defining the acceptable range for corneal reflex in the B-scans obtained in RS mode.

12. The method according to claim 11, wherein, for determining the axial lengths from the B-scan in RS mode from the B-scans in AS mode, a reference value is already determined for the axial position of the corneal reflex and an acceptable range for corneal reflex in the B-scans taken in RS mode is defined, readings outside the acceptable range being excluded from the aggregation.

13. The method according to claim 4, wherein a consistency of the aggregated axial lengths from AS and RS mode are checked so that a difference between the two absolute values may not exceed a defined tolerance.

* * * * *